(12) United States Patent
Tsai et al.

(10) Patent No.: US 7,508,519 B2
(45) Date of Patent: Mar. 24, 2009

(54) APPARATUS FOR SENSING PLURAL GASES

(75) Inventors: Ming-Lang Tsai, Donggang Town (TW); Jin-Sheng Chang, Kaohsiung (TW); Yii-Tay Chiou, Kaohsiung (TW); Chun-Hsun Chu, Tainan (TW)

(73) Assignee: Industrial Technology Research Institute, Hsinchu (TW)

( * ) Notice: Subject to any disclaimer, the term of this patent is extended or adjusted under 35 U.S.C. 154(b) by 395 days.

(21) Appl. No.: 11/324,481

(22) Filed: Jan. 4, 2006

(65) Prior Publication Data
US 2007/0120057 A1    May 31, 2007

(30) Foreign Application Priority Data
Nov. 11, 2005    (TW) .............................. 94139552 A

(51) Int. Cl.
*G01N 21/00* (2006.01)
(52) U.S. Cl. .................................................... 356/437
(58) Field of Classification Search ................. 356/432, 356/434, 435, 437; 385/12, 39, 129
See application file for complete search history.

(56) References Cited

U.S. PATENT DOCUMENTS

| 4,661,320 A | * | 4/1987 | Ito et al. ........................ 422/86 |
| 5,550,375 A | | 8/1996 | Peters et al. ................. 250/343 |
| 5,610,400 A | | 3/1997 | Wechstrom ................. 250/345 |
| 6,067,840 A | * | 5/2000 | Chelvayohan et al. ....... 73/23.2 |
| 6,121,617 A | | 9/2000 | Hirayama .................... 250/343 |
| 6,392,234 B2 | | 5/2002 | Diekmann ............... 250/338.3 |
| 6,469,303 B1 | | 10/2002 | Sun ............................. 250/343 |
| 2002/0189945 A1 | * | 12/2002 | Ruggiero .................... 204/451 |

FOREIGN PATENT DOCUMENTS

| DE | 3525755 C1 | * | 8/1986 |
| TW | 587165 | | 5/2004 |
| TW | I237112 | | 8/2005 |

* cited by examiner

*Primary Examiner*—Hwa (Andrew) S Lee
*Assistant Examiner*—Jonathon D Cook
(74) *Attorney, Agent, or Firm*—WPAT. P.C.; Justin King

(57) ABSTRACT

The apparatus for sensing plural gases is substantially a gas sensor adopting planar lightwave circuit for constructing reference optical path and sensing optical path, which is a flat structure with abilities of high accuracy, long-term stability, and short response time. The gas sensor can be widely applied for monitoring the safety of a working environment, securing the safety of workers, alerting potential hazard in a factory, inspecting harmful materials in a specific area, testing leakage of a pipeline, inspecting waste gas exhausted from automobile/motorcycle, and monitoring the living quality of household environment.

24 Claims, 5 Drawing Sheets

APPARATUS FOR SENSING PLURAL GASES

FIELD OF THE INVENTION

The present invention relates to a gas sensor, and more particularly, to a sensing apparatus capable of detecting and monitoring at least a gas by the use of reference optical paths and sensing optical paths constructed from a planar lightwave circuit of the sensing apparatus.

BACKGROUND OF THE INVENTION

The quantitative and qualitative analysis of gases and their mixtures has been found to be vastly applied in the fields of global environment monitoring, household safety inspecting, greenhouse environmental control, chemical concentration control, and certain applications relating to aerospace industry, etc. Nowadays, it is common to use gas sensors for performing the quantitative and qualitative analysis of gases and their mixtures, since not only the cost of monitoring the gases and their mixtures and the testing cycles required to be performed in the monitoring can be reduced, but also a real-time monitoring of the gases and their mixtures can be achieved thereby. However, cross sensitivity problem is common to those currently available gas sensors, such as semiconductor oxide gas sensors, metal oxide gas sensors, electrochemical gas sensors and solid electrolyte gas sensors, which can cause the reliability and repeatability of a monitoring result performed by such gas sensor to be adversely affected, i.e. the aforesaid gas sensors will fail to measure the individual concentration of each target gases of the monitoring accurately. Although, a gas sensor consists of an array of sensors sensitive to different gases can be used for detecting and measuring a plurality of gases, the cross sensitivity problem still can not be eliminated. For solving the foregoing cross sensitivity problem, the ability of certain gases to absorb infrared radiation has been successfully utilized in developing optical instruments for gas sensing, that is, gases can be selectively detected by the utilization of an infrared sensor via their specific absorption in the infrared spectral range. Despite their functional superiority, the optical gas sensors were not initially popular due to their structural complexity and high manufacturing cost, especially as the size of the optical gas sensor is increasing with the increasing of the amount of optical parts and relating elements of the optical gas sensor needed for detecting and measuring a plurality of gases. Therefore, the optical gas sensor currently available can only be used to detect and measure a gas of the specific infrared spectral range of the gas sensor, that the optical gas sensor can not be adaptively controlled for detecting and measuring various harmful gases coexisted in a same environment.

Please refer to FIG. 1, which is a schematic illustration of a conventional optical gas sensor used for detecting a specific gas. The optical gas sensor 1 of FIG. 1 is comprised of an infrared radiation source 10, a reference light source 11, a chamber 12, a narrow-band optical filter 13 and a photodiode 14, wherein the reference light source 11 is disposed in the chamber 12 intermediate to the first and second ends of the chamber 12, that is, at a distance from the photodiode 14 less than the distance between infrared radiation source 10 and photodiode 14, and the narrow band optical filter 13 selected for a specific wavelength with respect to a gas to be sensed is mounted between the reference light source 11 and the photodiode 14. As the infrared radiation source 10 is emitting light of a defined wavelength range to be transmitted and reflected in the chamber 12, the gas to be sensed in the chamber 12 will absorb the emitted light while enabling the absorbed light of the specific wavelength to pass through the narrow band optical filter 13 to be received by the photodiode 14. Since the light of the specific wavelength emitted by the reference light source 11 is received by the photodiode 14 without having to travel across the chamber 12 filled of gas to be sensed and thus it is not subject to the absorption of the gas to be sensed, the gas to be sensed can be detected and the concentration of the same can be measured by comparing of the intensity of the light emitted form the reference light source 11, which is used as a reference value or initial value, with that of the light emitted from the infrared radiation source 10 after passing through the chamber 12. However, the use of the reference light source in this basic optical gas sensor configuration is to compensate for changes and deterioration of optical components with time and temperature. In practice, the reference light source is added to the sensor to correct for these potential problems.

There are many optical gas sensors currently available, such as those disclosed in U.S. Pat. No. 6,067,840, U.S. Pat. No. 6,469,303, U.S. Pat. No. 6,392,234, U.S. Pat. No. 5,610, 400, and U.S. Pat. No. 5,550,375. It is noted that those shown in U.S. Pat. No. 6,067,840, U.S. Pat. No. 6,469,303, U.S. Pat. No. 6,392,234, U.S. Pat. No. 5,610,400, and U.S. Pat. No. 5,550,375 are only suitable for detecting a specific gas while the reference light source for emitting reference light and the infrared radiation source for emitting testing light used in the device shown in U.S. Pat. No. 6,067,840 are two different light sources.

From the above description, there are four major shortcomings can be summed up as following:

(1) By having reference light and testing light to be emitted from two different light sources as those used in prior-art sensors, it is possible that one might not be able to distinct the initial value, being obtained from the reference light representing no target gas sensed, from a response value, being obtained from the testing light representing the existence of the target gas, since the two light sources might begin to deteriorate at different times. Therefore, it is preferred to have the reference light and the testing light to be emitted from a same light source so that the time of deterioration of the two is identical and thus the distinction between the initial value and the response value is ease to identify.

(2) It is known that the reflection index of a material/ atmosphere is varying along the change of ambient temperature, pressure or the properties of the material, and the change of reflection index will consequently cause the corresponding optical path to change. Hence, since the length of the optical path of the reference light is different from that of the testing light as those used in prior-art sensors while the initial value is subject to the influence of ambient temperature, pressure and the properties of the material, the accuracy and long-term stability of the gas sensor are reduced.

(3) The prior-art gas sensors can not be adapted for multi-gas testing.

(4) The structure of the prior-art gas sensor can not be flattened.

Therefore, it is in great need to have an apparatus for sensing plural gases that is capable of overcoming the foregoing problems.

SUMMARY OF THE INVENTION

The primary object of the invention is to provide an apparatus for sensing plural gases, which is free from the cross sensitivity problem while it is being used to sense plural gases, and is free from the influences of ambient temperature change, ambient pressure change, wave-guide material property change and the deterioration of light sources so as to increase the accuracy and long-term stability of the aforesaid apparatus, and is a flat gas sensor by the adoption of planar lightwave circuit.

To achieve the above objects, the present invention provides an apparatus for sensing plural gases, which comprises a photogenerator, a planar light wave circuit, and at least a photodetector. The photogenerator is utilized for emitting a signal light. The planar lightwave circuit, having a sensing pathway and a reference pathway, is coupled to the photogenerator by an input port thereof for enabling the same to receive the signal light and thus generate a sensing signal and a reference signal in respective. The sensing pathway and the reference pathway respectively have at least an optic gap and at least an output port. The at least one detector is disposed at one of the output ports of the reference pathway or the output ports of the sensing pathway for converting the sensing/reference signal into an electric signal.

Preferably, the photogenerator is one device selected from the group consisting of an edge-emitting laser diode, a surface-emitting laser diode, and a light emitting diode.

Preferably, the interval of the optic gap formed in the sensing pathway is the same as that in the reference pathway, and the length of the sensing pathway is the same as that of the reference pathway.

Preferably, each optic gap of the reference pathway is sealed by an isolating element.

Preferably, there can be a filter being disposed between each photodetector and the output port corresponding thereto.

Moreover, the apparatus for sensing plural gases further comprises a substrate for carrying the photogenerator, the planar lightwave circuit and the photodetectors, wherein the planar lightwave circuit is formed directly on the surface of the substrate, and is made of a material selected from the group consisting of a semiconductor material, a polymer, and a metal.

Preferably, the apparatus for sensing plural gases further comprises a separation film for isolating dust and dirt while allowing target gases to pass through.

Preferably, the apparatus for sensing plural gases further comprises a control circuit, coupled respectively to the photogenerator and the photodetectors.

In a preferred embodiment of the invention, the present invention provides an apparatus for sensing plural gases, which comprises a plurality of photogenerators, a plurality of planar light wave circuits, and a plurality of photodetectors. Each photogenerators is capable of emitting a signal light. Each planar light wave circuit has a sensing pathway and a reference pathway and is coupled to one of the photogenerators by an input port thereof for enabling the same to receive the signal light and thus generate a sensing signal and a reference signal, respectively. The sensing pathway and the reference pathway respectively have at least an optic gap and at least an output port. Each photodetector is disposed at one of the output ports of the reference pathway or the output ports of the sensing pathway for converting the corresponding sensing/reference signal into an electric signal.

Preferably, the two lights emitted from any two neighboring photogenerators of the plural photogenerators can be specified to a condition selected from the group consisting of: the condition of the same wavelength and the condition of different wavelengths.

Preferably, the apparatus for sensing plural gases further comprises at least an intermittent photogenerator, each being disposed between any of the two neighboring photogenerators; wherein a planar lightwave circuit coupled to each intermittent photogenerator is connected to the planar lightwave circuits coupled to the two neighboring photogenerators, and the lights emitted from the intermittent photogenerator and those of the two photogenerators neighboring thereto can be specified to a condition selected from the group consisting of: the condition of the same wavelength and the condition of different wavelengths.

Other aspects and advantages of the present invention will become apparent from the following detailed description, taken in conjunction with the accompanying drawings, illustrating by way of example the principles of the present invention.

DESCRIPTION OF THE PREFERRED EMBODIMENT

For your esteemed members of reviewing committee to further understand and recognize the fulfilled functions and structural characteristics of the invention, several preferable embodiments cooperating with detailed description are presented as the follows.

Figure 1:
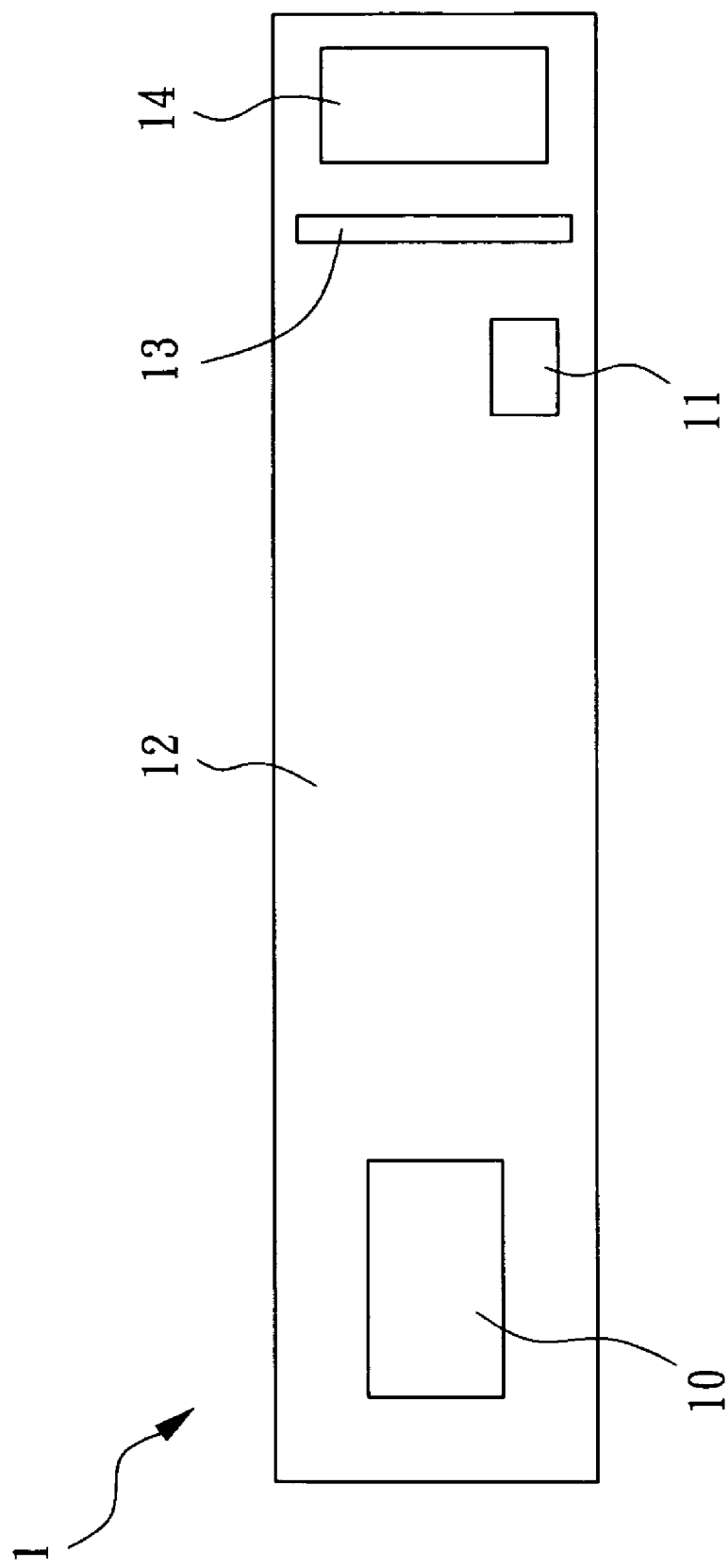
FIG. 1 is a schematic illustration of a conventional optical gas sensor used for detecting a specific gas
Figure 2A:
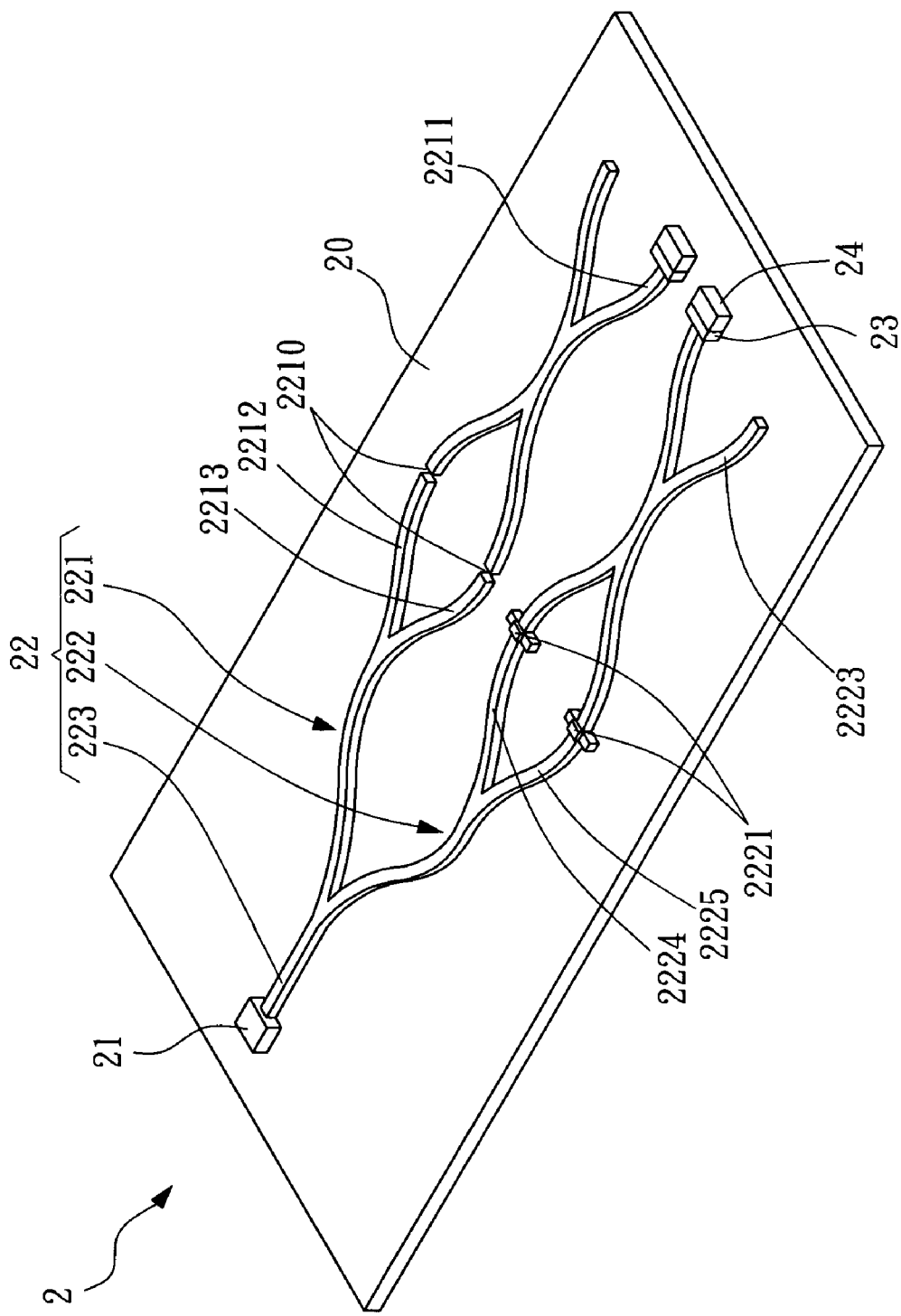
FIG. 2A is a schematic illustration of an apparatus for sensing plural gases according to a preferred embodiment of the invention.

Please refer to FIG. 2A, which is a schematic illustration of an apparatus for sensing plural gases according to a preferred embodiment of the invention. The apparatus for sensing plural gases 2 of FIG. 2A is formed on a substrate 20, which can be made of a semiconductor material, a polymer, a metal or a flexible material. The apparatus 2 comprises a photogenerator 21, a planar lightwave circuit 22, a filter 23 and at least a photodetectors 24. In this preferred embodiment, there are two photodetectors, however, the number of the photodetectors is not limited thereby. The planar lightwave circuit 22 is coupled to the photogenerator 21 by an input port 223 thereof for enabling the same to receive the signal light emitted from the photogenerator 21. It is noted that photogenerator 21 can be an edge-emitting laser diode, a surface-emitting laser diode, or a light emitting diode, that is chosen with respect to the type of gas to be sensed.

Figure 3A:
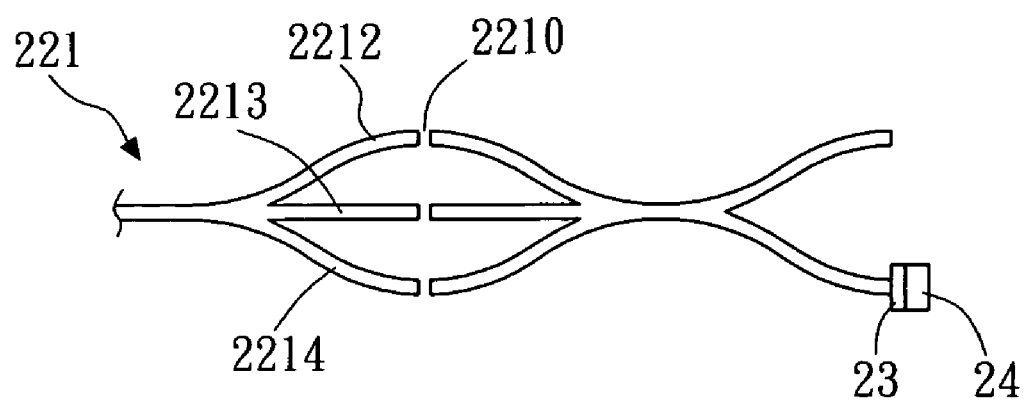
FIG. 3A is a schematic diagram showing optic gaps being formed in the sensing pathway according to a preferred embodiment of the invention.
Figure 3B:
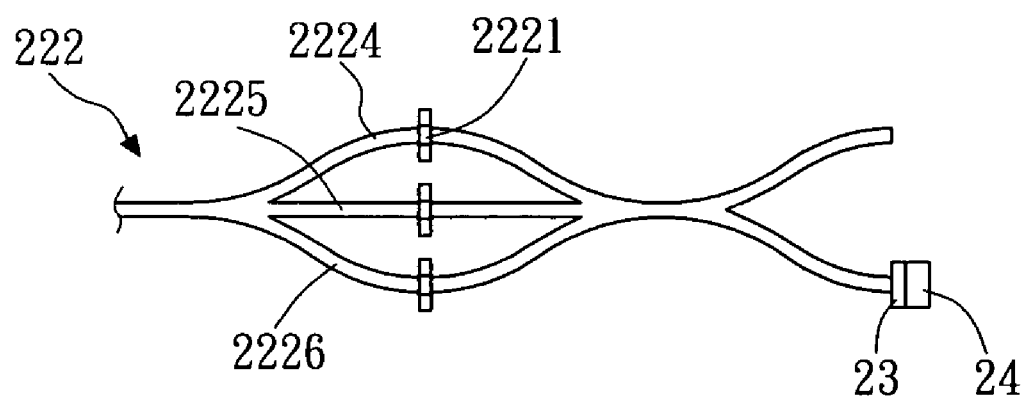
FIG. 3B is a schematic diagram showing optic gaps being formed in the reference pathway according to a preferred embodiment of the invention.

The planar lightwave circuit 22 further has a sensing pathway 221 and a reference pathway 222. As seen in FIG. 2A, the sensing pathway 221 is split into two waveguide branches 2212, 2213, each having an optic gap 2210 formed thereon, and then the two waveguide branches 2212, 2213 are merged into a pathway. Moreover, the sensing pathway 221 has at least an output port 2211, where a filter 23 and a photodetector 24 is disposed by arranging the filter 23 at a position between the output port 2211 and the photodetector 24. Similarly, the reference pathway 222 also is split into two waveguide branches 2224, 2225, each having an optic gap 2220 formed thereon, and then the two waveguide branches 2224, 2225 are merged into a pathway. Moreover, the reference pathway 222 also has at least an output port 2223, where a filter 23 and a photodetector 24 is disposed by arranging the filter 23 at a position between the output port 2223 and the photodetector 24. It is noted that the number of waveguide branch, such as the waveguide branches 2212, 2213 of the sensing pathway 221 and the waveguide branches 2224, 225 of the reference pathway 222, is not limited by two as that shown in the embodiment of FIG. 2A, that the number of waveguide branch can be three for both the sensing pathway 221 and the reference pathway 222 as those shown in FIG. 3A and FIG. 3B. The purpose of arranging waveguide branches in a pathway is to increase the contact between the signal light and the gases to be sensed so that the accuracy of a measurement using the apparatus can be improved.

In this preferred embodiment of the invention, the interval of the optic gap 2210 formed in the sensing pathway 221 is the same as that in the reference pathway 222, and the length of the sensing pathway 221 is the same as that of the reference pathway 222.

Figure 2B:
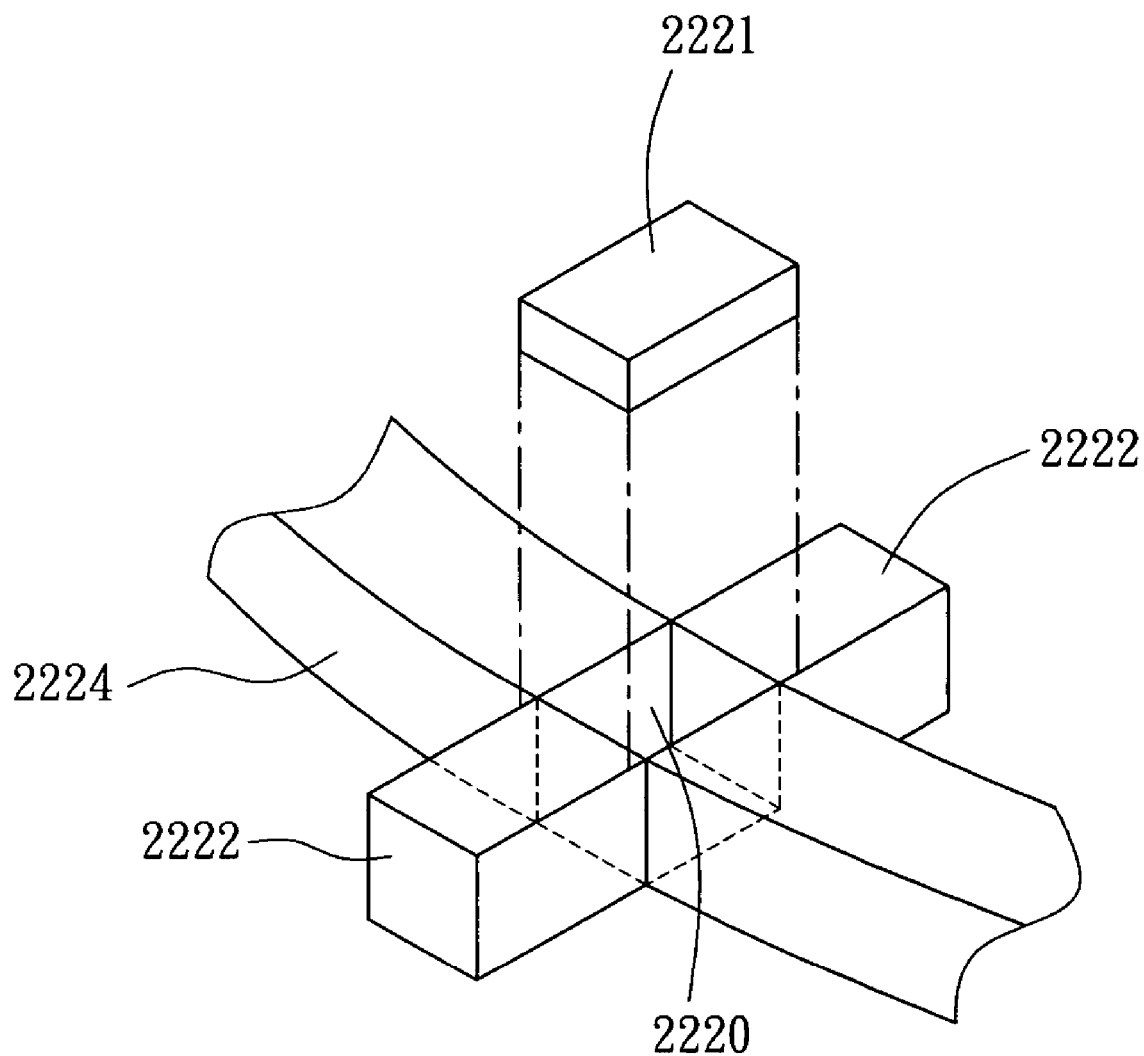
FIG. 2B is a schematic illustration of an isolating element used in the apparatus for sensing plural gases of the invention.

Please refer to FIG. 2B, which is a schematic illustration of an isolating element used in the apparatus for sensing plural gases of the invention. The arrangement of the reference pathway 222 in the planar lightwave circuit 22 is to provide a reference for a measurement, whereas gas used to obtain the reference is air. In order to prevent the gases to be sensed from mixing with air, an isolating element is used to seal each optic gap 2220 on each waveguide branches 2224, 2225 of the reference pathway 222, that the isolating element is comprised of two isolating block 2222, used to filled the two sides of an optic gap, and an isolating plate 2221, used to cover the top of the optic gap. The apparatus of this embodiment further comprises a control circuit coupled respectively to the photogenerator 21 and the photodetectors 24. The control circuit is used to control the signal light to be emitted by the photogenerator 21 and to process the electric signals generated by the photodetectors 24. Operationally, the light emitted by the photogenerator 21 will be fed into the planar light wave circuit 22 through the input port 223 thereof, and then the light is split and guided by the operation of the planar light wave circuit 22 to be fed into the sensing pathway 221 and the reference pathway 222. The light entering the sensing pathway 221 will contact the gases to be sensed at the optic gaps 2210 thereof where the intensity of the light is varied by the absorption of the gases acting on the light, and the intensity-varied light pass the filter 23 and enter the photodetector 24 for enabling the photodetector 24 to issue a response signal accordingly. On the other hand, the light entering the reference pathway 222 will be blocked from contacting the gases to be sensed since the optic gaps thereof is sealed by the isolating element 2221 so that the intensity of the light is maintained unchanged, and then the intensity-unchanged light pass the filter 23 and enter the photodetector 24 for enabling the photodetector 24 to issue a reference signal accordingly. The filter 23 is used to isolate lights other than the intended light emitted from the photogenerator 21 from entering the photodetector 24, and the photodetector 24 is used to convert the received response/reference signal into a corresponding electric signal. In addition, in order to prevent the accuracy of the apparatus 2 of the invention to be adversely affected by the pollution of dust or dirt depositing in the optic gaps, a separation film is provided for isolating dust and dirt from entering the apparatus 2 while allowing the plural gases to pass through.

Figure 4:
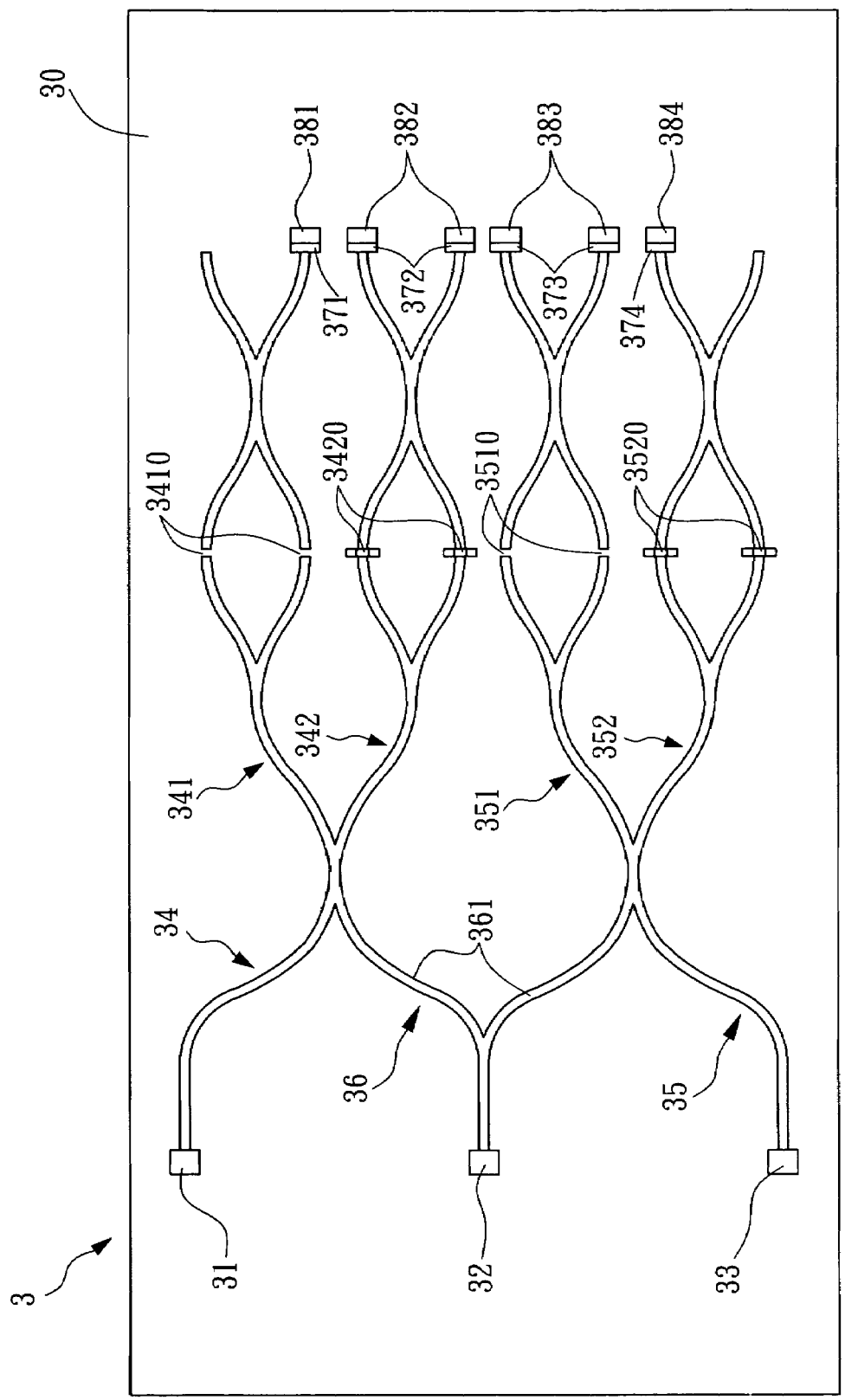
FIG. 4 is a schematic illustration of an apparatus for sensing plural gases according to another preferred embodiment of the invention.

Please refer to FIG. 4, which is a schematic illustration of an apparatus for sensing plural gases according to another preferred embodiment of the invention. The apparatus for sensing plural gases 3 is formed on a substrate 30, that is basically used for detecting three different gases. The structure of the apparatus 3 is similar to the apparatus 2 shown in FIG. 2A and the only difference between the two is that the apparatus 3 has three planar lightwave circuit and the devices corresponding thereto. The apparatus 3 has a first planar lightwave circuit 34, a second planar lightwave circuit 35 and a third planar lightwave circuit 36, wherein the input port of the first planar lightwave circuit 34 is coupled to a first photogenerator 31, and the input port of the second planar lightwave circuit 35 is coupled to a third photogenerator 33, and the input port of the third planar lightwave circuit 36 is coupled to a intermittent photogenerator 32. Furthermore, the substrate 30 can be made of a semiconductor material, a polymer, a metal or a flexible material; the wavelengths of the lights emitted from the first photogenerator 31, the intermittent photogenerator 32 and the third photogenerator 33 can be different from each other and each of the three photogenerator 31, 32, 33 can be a device selected from the group consisting of an edge-emitting laser diode, a surface-emitting laser diode, and a light emitting diode. It is noted that the wavelength of light emitted by the three respectively is chosen with respect to the type of gas to be sensed.

The third planar lightwave circuit 36 is split into two waveguide branches 361, which are connected respectively to the first planar lightwave circuit 34 and the second planar lightwave circuit 35. As seen in FIG. 4, the configuration of the first planar lightwave circuit 34 is the same as that of the second planar lightwave circuit 35, that the first planar lightwave circuit 34 has a sensing pathway 341 and a reference pathway 342 while the second planar lightwave circuit 35 has a sensing pathway 351 and a reference pathway 352. Each of the two sensing pathways 341, 351 is split into two waveguide branches, each having an optic gap formed thereon, i.e. optic gap 3410 of the first planar lightwave circuit 34 and the optic gap 3510 for the second planar lightwave circuit 35, and then the two waveguide branches are merged into a pathway. Moreover, each of the two sensing pathways 341, 351 has at least an output port, where a filter and a photodetector is disposed by arranging the filter at a position between the output port and the photodetector, i.e. the filter 371 and the photodetector 381 for the sensing pathway 341 and the filter 373 and the photodetector 383 for the sensing pathway 351. Similarly, each of the two reference pathways 342, 352 also is split into two waveguide branches, each having an optic gap formed thereon, and then the two waveguide branches are merged into a pathway. Moreover, each of the reference pathways 342, 352 also has at least an output port, where a filter and a photodetector is disposed by arranging the filter at a position between the output port and the photodetector, i.e. the filter 372 and the photodetector 382 for the reference pathway 342 and the filter 374 and the photodetector 384 for the reference pathway 352. In order to prevent the gases to be sensed from mixing with air, an isolating element, i.e. the two isolating elements 3420, 3520 shown in FIG. 4, is used to seal each optic gap on each waveguide branches of the reference pathways 342, 352. It is noted that the principle of detection of the apparatus shown in FIG. 4 is the same as that shown in FIG. 2A, and thus is not described further herein.

By the proper application of planar lightwave circuit, the apparatus of the invention has advantages list as following: (1) The structure of the apparatus can be flattened for enabling the same to be a thin gas sensor; (2) the apparatus of the invention can be adapted to detect and measure plural gases while the number of gases can be numerous; (3) the signal response time is shortened; (4) the apparatus of the invention can have high accuracy and better long-term stability.

From the above description, it is noted that all the number of the device used in the apparatus for sensing plural gases of the present invention, such as the numbers of the input port of the planar lightwave circuit, the number of the reference pathway, the number of the sensing pathway, and so on, are only used for illustration and are not limited thereby. In summary that this invention has been disclosed and illustrated with reference to particular embodiments, the principles involved are susceptible for use in numerous other embodiments that will be apparent to persons skilled in the art. Consequently, the present invention has been examined to be progressive and has great potential in commercial applications.

While the preferred embodiment of the invention has been set forth for the purpose of disclosure, modifications of the disclosed embodiment of the invention as well as other embodiments thereof may occur to those skilled in the art. Accordingly, the appended claims are intended to cover all embodiments which do not depart from the spirit and scope of the invention.

What is claimed is:

1. An apparatus for sensing plural gases, comprising:
a photogenerator, for emitting a signal light;
a planar lightwave circuit having a sensing pathway and a reference pathway, being coupled to the photogenerator by an input port thereof for enabling the sensing pathway and the reference pathway to receive the signal light and thus generate a sensing signal and a reference signal respectively; wherein the sensing pathway and the reference pathway respectively has at least an optic gap and at least an output port; and
at least a photodetector, each being disposed at one of the output port selected form the group consisting of the output ports of the reference pathway and the output ports of the sensing pathway, for converting the sensing/reference signal into an electric signal;
wherein the sensing pathway and the reference pathway have at least two waveguide branches respectively, and the waveguide branches of the sensing pathway and the waveguide branches of the reference pathway are merged with the input port means for sensing the gas in said optic gap in the sensing pathway using the electric signals from the photodetector in the sensing an reference pathways.

2. The apparatus of claim 1, wherein the photogenerator is a device selected from the group consisting of an edge-emitting laser diode, a surface-emitting laser diode, and a light emitting diode.

3. The apparatus of claim 1, wherein the interval of the optic gap formed in the sensing pathway is the same as that in the reference pathway.

4. The apparatus of claim 1, wherein each optic gap of the reference pathway is sealed by an isolating element.

5. The apparatus of claim 1, wherein the length of the sensing pathway is the same as that of the reference pathway.

6. The apparatus of claim 1, wherein a filter is disposed at a position between each photodetector and the output port corresponding thereto.

7. The apparatus of claim 1, further comprising a substrate for carrying the photogenerator, the planar lightwave circuit and the photodetectors; wherein the planar lightwave circuit is formed directly on the surface of the substrate.

8. The apparatus of claim 7, wherein the substrate is made of a material selected from the group consisting of a semiconductor material, a polymer, and a metal.

9. The apparatus of claim 1, further comprising a separation film for isolating dust and dirt while allowing the plural gases to pass through.

10. The apparatus of claim 1, further comprising a control circuit, coupled respectively to the photogenerator and the photodetectors.

11. An apparatus for sensing plural gases, comprising:
a plurality of photogenerators, each capable of emitting a signal light;
a plurality of planar lightwave circuits, each having a sensing pathway and a reference pathway and being coupled to one of the photogenerators by an input port thereof for enabling the same to receive the signal light and thus generate a sensing signal and a reference signal in respective; wherein the sensing pathway and the reference pathway respectively has at least an optic gap and at least an output port; and
a plurality of photodetectors, each being disposed at one of the output ports selected from the group consisting of the output ports of the reference pathway and the output ports of the sensing pathway, for converting the corresponding sensing/reference signal into an electric signal;
wherein the sensing pathway and the reference pathway have at least two waveguide branches respectively, and the waveguide branches of the sensing pathway and the waveguide branches of the reference pathway are merged with the input port means for sensing the gas in said optic gap in the sensing pathways using the electric signals from the photodetectors in the sensing and reference pathways.

12. The apparatus of claim 11, wherein the two lights emitted from any two neighboring photogenerators of the plural photogenerators have different wavelengths.

13. The apparatus of claim 11, further comprising at least an intermittent photogenerator, each being disposed between any of the two neighboring photogenerators; wherein a planar lightwave circuit coupled to each intermittent photogenerator is connected to the planar lightwave circuits coupled to the two neighboring photogenerators.

14. The apparatus of claim 13, wherein the lights emitted from the intermittent photogenerator and those of the two photogenerators neighboring thereto have different wavelengths.

15. The apparatus of claim 13, wherein the intermittent photogenerator is a device selected from the group consisting of an edge-emitting laser diode, a surface-emitting laser diode, and a light emitting diode.

16. The apparatus of claim 11, wherein the photogenerator is a device selected from the group consisting of an edge-emitting laser diode, a surface-emitting laser diode, and a light emitting diode.

17. The apparatus of claim 11, wherein the interval of the optic gap formed in the sensing pathway is the same as that in the reference pathway.

18. The apparatus of claim 11, wherein each optic gap of the reference pathway is sealed by an isolating element.

19. The apparatus of claim 11, wherein the length of the sensing pathway is the same as that of the reference pathway.

20. The apparatus of claim 11, wherein a filter is disposed at a position between each photodetector and the output port corresponding thereto.

21. The apparatus of claim 11, wherein further comprising a substrate for carrying the plural photogenerators, the plural planar lightwave circuits and the plural photodetectors; wherein the plural planar lightwave circuits are formed directly on the surface of the substrate.

22. The apparatus of claim 21, wherein the substrate is made of a material selected from the group consisting of a semiconductor material, a polymer, and a metal.

23. The apparatus of claim 11, further comprising a separation film for isolating dust and dirt while allowing the plural gases to pass through.

24. The apparatus of claim 11, further comprising a control circuit, coupled respectively to the plural photogenerators and the plural photodetectors.

* * * * *